US00PP13161P2

(12) United States Plant Patent
Bloom et al.

(10) Patent No.: US PP13,161 P2
(45) Date of Patent: Oct. 29, 2002

(54) CAMPANULA PLANT NAMED 'CAMGOOD'

(75) Inventors: Adrian Bloom, Diss (GB); Paul Gooderham, Diss (GB)

(73) Assignee: Blooms of Bressingham Ltd., Diss (GB)

( * ) Notice: Subject to any disclaimer, the term of this patent is extended or adjusted under 35 U.S.C. 154(b) by 81 days.

(21) Appl. No.: 09/840,808

(22) Filed: Apr. 25, 2001

(51) Int. Cl.[7] ..... A01H 5/00
(52) U.S. Cl. ..... Plt./263
(58) Field of Search ..... Plt./263

*Primary Examiner*—Kent L. Bell
(74) *Attorney, Agent, or Firm*—C. A. Whealy

(57) ABSTRACT

A distinct cultivar of Campanula plant named 'Camgood', characterized by its rapid growth rate; clumping and spreading growth habit; freely flowering habit; long flowering period; and violet blue campanulate flowers.

1 Drawing Sheet

BOTANICAL CLASSIFICATION/CULTIVAR DESIGNATION

*Campanula poscharskyana* cultivar 'Camgood'.

BACKGROUND OF THE INVENTION

The present Invention relates to a new and distinct cultivar of Campanula plant, botanically known as *Campanula poscharskyana*, is marketed under the trade name Blue Waterfall, and hereinafter referred to by the name 'Camgood'.

The new Campanula originated from a cross made by the Inventors of the *Campanula poscharskyana* cultivar 'Stella', not patented, as the female, or seed parent, with an unnamed selection of *Campanula poscharskyana*, not patented, as the male, or pollen, parent. The cultivar 'Camgood' was discovered and selected by the Inventors as a flowering plant within the progeny of the stated cross in a controlled environment in 1996 in Bressingham, United Kingdom.

Asexual reproduction of the new cultivar by divisions and basal cuttings taken at Bressingham, United Kingdom, since June, 1996, has shown that the unique features of this new Campanula are stable and reproduced true to type in successive generations.

SUMMARY OF THE INVENTION

Plants of the cultivar 'Camgood' have not been observed under all possible environmental conditions. The phenotype may vary somewhat with variations in environment such as temperature, light intensity, daylength, fertility type or rate, and/or water status without, however, any variance in genotype.

The following traits have been repeatedly observed and are determined to be the unique characteristics of 'Camgood'. These characteristics in combination distinguish 'Camgood' as a new and distinct cultivar:

1. Rapid growth rate, vigorous growth habit.
2. Clumping and spreading growth habit, dense plants.
3. Freely flowering habit.
4. Long flowering period.
5. Violet blue campanulate flowers.

Plants of the new Campanula differ from plants of the parents in the following characteristics:

1. Plants of the new Campanula have larger leaves than plants of the parents.
2. Plants of the new Campanula are more outwardly spreading in habit than plants of the parents.
3. Plants of the new Campanula are more freely flowering and have larger flowers than plants of the parents.
4. Flowers of plants of the new Campanula are more blue in color than flowers of plants of the parents.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ from the color values cited in the detailed botanical description which accurately describe the colors of the new Campanula.

The photograph comprises a side perspective view of a typical plant of 'Camgood' grown in the landscape for two growing seasons.

DETAILED BOTANICAL DESCRIPTION

In the following description, color references are made to The Royal Horticultural Society Colour Chart except where general terms of ordinary dictionary significance are used. Plants were grown in Bressingham, United Kingdom under field conditions which closely approximate commercial production conditions. During the production of the plants, day temperatures ranged from 5 to 28° C. and night temperatures ranged from −8 to 15° C. Plants used for the description were grown for two growing seasons in 5-liter containers.

Parentage:

*Female, or seed, parent.*—*Campanula poscharskyana* cultivar 'Stella', not patented.

*Male, or pollen, parent.*—Unnamed selection of *Campanula poscharskyana*, not patented.

Propagation:

*Type.*—By basal cuttings.

*Time to initiate roots.*—About 10 days at 20° C.

*Time to produce a rooted cutting.*—About 30 days at 20° C.

*Root description.*—Fibrous, thin, grayed white in color.

*Rooting habit.*—Freely branching, dense.

Plant description:

*Rate of growth.*—Rapid growth rate; during one growing season in United Kingdom, plants of the new Campanula will grow at least 100 cm in stem length. Vigorous.

*Form.*—Low spreading and clumping perennial; stems arise from the root crown.

*Usage.*—Appropriate for use as a border plant, as a ground cover, and in containers.

*Plant height, soil level to top of plant plane.*—About 15 cm.

*Plant width.*—About 100 cm.

*Stem description.*—Orientation: Trailing, prostrate. Quantity: More than 30 per plant. Length: About 60 cm. Texture: Smooth, glabrous. Color: 144B.

*Foliage description.*—Leaves simple, basal, generally symmetrical and long persisting. Length: About 4.5 cm. Width: About 4 cm. Shape: Cordate. Apex: Mucronulate. Base: Cordate. Margin: Biserrate. Texture, both surfaces: Slightly pubescent. Venation pattern: Lacinate. Color: Young and fully expanded foliage, upper surface: 143A; venation, 139C. Young and fully expanded foliage, lower surface: 143C; venation, 138A. Petiole: Length: About 15 cm. Diameter: About 2 mm. Texture: Smooth. Color: 144C.

Flower description:

*Flower type and habit.*—Single star-shaped campanulate flowers arranged in panicles. Flowering stems, prostrate and trailing; flowers, face upright. Flowers persistent.

*Fragrance.*—Not detected.

*Natural flowering season.*—Continuously flowering from May to October in Bressingham, United Kingdom.

*Quantity.*—Freely flowering with about 80 flowers and flower buds per stem or about 2,600 flowers per plant.

*Flower longevity.*—About 3 to 5 days on the plant.

*Flower diameter.*—About 4 cm.

*Flower depth* (*height*).—About 1.5 cm.

*Flower buds.*—Length: About 1.5 cm. Diameter: About 6 mm. Shape: Ovate. Color: 92C.

*Petals.*—Arrangement/appearance: Five petals in a single whorl, fused at the base; star-shaped. Length: About 2 cm. Width: About 7 mm. Shape: Lanceolate. Apex: Acute. Margin: Entire. Texture: Smooth. Color: Upper surface, when opening and fully opened: 92A; color does not fade with subsequent development. Lower surface, when opening and fully opened: 91A.

*Sepals.*—Quantity/arrangement: Five sepals in a single whorl, fused at the base; star-shaped. Length: About 1 cm. Diameter: About 4 mm. Shape: Lanceolate. Apex: Acute. Margin: Serrate. Color, both surfaces: 138B flushed with 183C.

*Peduncles.*—Length: About 60 cm. Diameter: About 4 mm. Strength: Weak. Angle: Prostrate, trailing. Color: 138A.

*Pedicels.*—Length: About 2 cm. Diameter: About 1 mm. Strength: Moderately strong. Angle: Acute. Color: 138A.

*Reproductive organs.*—Androecium: Quantity of stamens: Four per flower. Anther shape: Linear. Anther length: About 5 mm. Anther color: 162C. Pollen amount: Scarce. Pollen color: 162C. Gynoecium: Quantity of pistils: One per flower. Pistil length: About 1.5 cm. Stigma shape: Rounded. Stigma color: 92A. Style length: About 4 mm. Style color: 92A. Ovary color: 155C.

*Seed.*—Quantity: About 5 to 8 seeds per inflorescence. Length: About 1 mm. Diameter: About 0.5 mm. Color: 172B.

Disease/pest resistance: Under commercial production conditions, plants of the new Campanula have not been noted to be resistant to pathogens or pests common to Campanula.

Weather/temperature tolerance: Plants of the new Campanula have been observed to tolerate rain, wind, and temperatures from −8 to 28° C. in Bressingham, United Kingdom.

It is claimed:

1. A new and distinct cultivar of Campanula plant named 'Camgood', as illustrated and described.

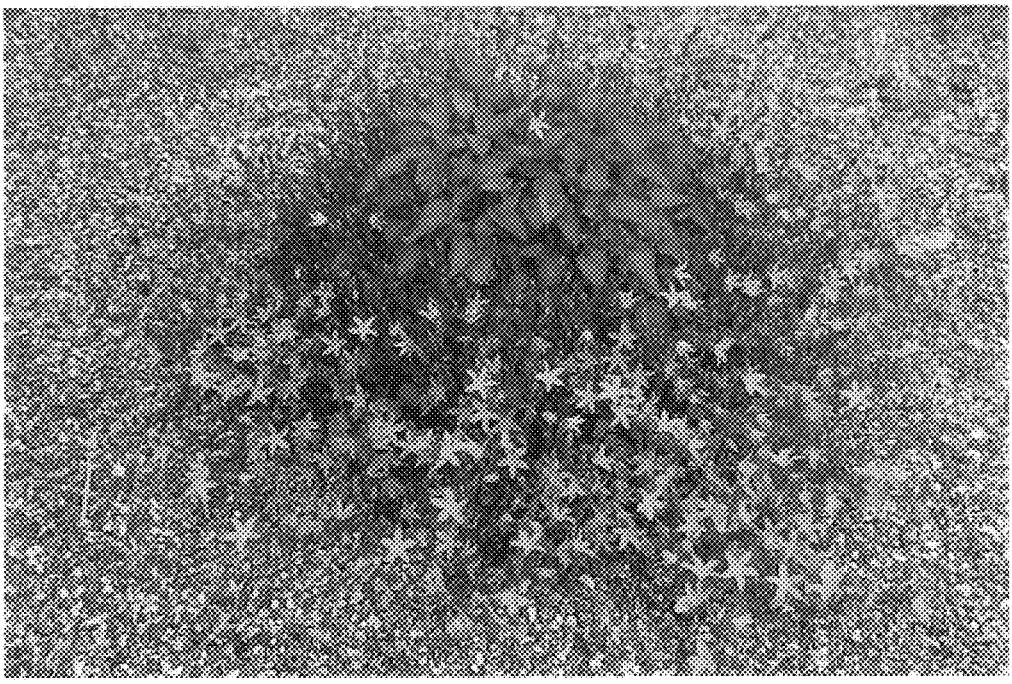

* * * * *